(12) United States Patent
Childress et al.

(10) Patent No.: US 10,918,748 B2
(45) Date of Patent: Feb. 16, 2021

(54) DEPLOYABLE ULTRAVIOLET LIGHT SANITIZING SYSTEMS AND METHODS

(71) Applicant: THE BOEING COMPANY, Chicago, IL (US)

(72) Inventors: Jamie Childress, Mercer Island, WA (US); Teresa A. King, Bothell, WA (US)

(73) Assignee: THE BOEING COMPANY, Chicago, IL (US)

( * ) Notice: Subject to any disclaimer, the term of this patent is extended or adjusted under 35 U.S.C. 154(b) by 825 days.

(21) Appl. No.: 15/259,685

(22) Filed: Sep. 8, 2016

(65) Prior Publication Data

US 2018/0064833 A1 Mar. 8, 2018

(51) Int. Cl.
*A61L 2/10* (2006.01)
*A61L 2/24* (2006.01)
*B64D 11/02* (2006.01)

(52) U.S. Cl.
CPC .................... *A61L 2/10* (2013.01); *A61L 2/24* (2013.01); *B64D 11/02* (2013.01); *A61L 2202/11* (2013.01); *A61L 2202/14* (2013.01); *A61L 2202/25* (2013.01)

(58) Field of Classification Search
CPC .................... A61L 2/10; A61L 2/24
See application file for complete search history.

(56) References Cited

U.S. PATENT DOCUMENTS

| 4,819,276 | A | 4/1989 | Stevens | |
| 2007/0164232 | A1 | 7/2007 | Rolleri | |
| 2010/0032589 | A1* | 2/2010 | Leben | A61L 2/10 250/504 R |
| 2014/0059796 | A1* | 3/2014 | Boodaghians | A61L 2/10 15/339 |
| 2014/0115764 | A1 | 5/2014 | Cheng | |
| 2015/0086420 | A1* | 3/2015 | Trapani | A61L 2/202 422/24 |
| 2015/0190538 | A1 | 7/2015 | Olvera | |

FOREIGN PATENT DOCUMENTS

| CN | 2155875 | 2/1994 |
| CN | 1430522 | 7/2003 |
| CN | 2624896 | 7/2004 |
| CN | 2688291 | 3/2005 |

(Continued)

OTHER PUBLICATIONS

Extended European Search Report for EP 17189449.6-1754, dated Dec. 7, 2017.

(Continued)

*Primary Examiner* — Sean E Conley
(74) *Attorney, Agent, or Firm* — The Small Patent Law Group LLC; Joseph M. Butscher (57) ABSTRACT

An ultraviolet (UV) light sanitizing system and method are configured to sanitize at least one surface within an enclosed space. The UV light sanitizing system includes a UV light assembly that is selectively moveable between a stowed position and a deployed position. The UV light assembly is stowed within a stowage chamber connected to the enclosed space in the stowed position. The UV light assembly deploys out of the stowage chamber and into the enclosed space in the deployed position.

10 Claims, 10 Drawing Sheets

(56) References Cited

FOREIGN PATENT DOCUMENTS

| CN | 200977291 | 11/2007 |
|---|---|---|
| CN | 200984335 | 12/2007 |
| CN | 103959429 | 7/2014 |
| CN | 204193104 | 3/2015 |
| EP | 2492195 | 8/2012 |
| EP | 2772272 | 9/2014 |
| EP | 2891205 | 7/2015 |
| WO | WO 2014036217 | 3/2014 |

OTHER PUBLICATIONS

Notification of First Office Action for CN App. No. 2017105742660, dated Jun. 3, 2020 (and English translation).

* cited by examiner

DEPLOYABLE ULTRAVIOLET LIGHT SANITIZING SYSTEMS AND METHODS

FIELD OF THE DISCLOSURE

Embodiments of the present disclosure generally relate to ultraviolet light sanitizing systems and methods, and, more particularly, to deployable ultraviolet light sanitizing systems and methods, such as may be used within lavatories of aircraft.

BACKGROUND OF THE DISCLOSURE

Commercial aircraft are used to transport passengers between various locations. A typical commercial aircraft includes one or more lavatories within an internal cabin.

Systems are currently being developed to disinfect or otherwise sanitize surfaces within aircraft lavatories that use ultraviolet (UV) light. For example, it has been found that far UV light efficiently disinfects exposed surfaces within a lavatory.

In order to effectively sanitize a surface within a lavatory, a UV light assembly may be fixed in close proximity to the surface. For example, a UV light assembly may be spaced from a toilet within a lavatory a distance of less than one foot. As can be appreciated, however, positioning a UV light assembly within close proximity to a component may interfere with use of the component. In general, a UV light assembly may undesirably protrude into a confined space of an aircraft lavatory.

As another option, far UV lamps may be secured at a greater distance from a component so as not to interfere with use of the component. However, in order to effectively sanitize the component, a particular magnitude of light energy is required. With many light sources, light energy is greatest proximate to the source due to dispersal of light and absorption of light with respect to air, for example. Thus, the power supplied to the UV light assembly is typically increased as the distance of the component is increased.

SUMMARY OF THE DISCLOSURE

A need exists for a system and method for efficiently and effectively sanitizing a surface of a component. A need exists for a system and method for operating a UV light assembly to sanitize a component without interfering with use of the component by an individual.

With those needs in mind, certain embodiments of the present disclosure provide an ultraviolet (UV) light sanitizing system that is configured to sanitize at least one surface within an enclosed space. The UV light sanitizing system includes a UV light assembly that is selectively moveable between a stowed position and a deployed position. The UV light assembly is stowed within a stowage chamber connected to the enclosed space in the stowed position. The UV light assembly deploys out of the stowage chamber and into the enclosed space in the deployed position.

The UV light assembly is closer to the surface(s) in the deployed position than the stowed position. In at least one embodiment, the UV light assembly remains in the stowed position when the enclosed space is occupied by an individual.

The UV light assembly may include a housing, and a shield surrounding at least a portion of the housing. The shield is configured to block electromagnetic interference. The UV light assembly may also include a UV light emitter. A cage may surround at least a portion of the UV light emitter.

In at least one embodiment, an actuator is operatively coupled to the UV light assembly. The actuator is configured to move the UV light assembly between the stowed position and the deployed position.

In at least one embodiment, a UV light control unit is in communication with the UV light assembly. The UV light control unit is configured to control movement of the UV light assembly between the stowed position and the deployed position. The UV light control unit is configured to operate the UV light assembly during a sanitizing cycle in which the UV light assembly emits sanitizing UV light onto the surface(s).

The UV light sanitizing system may include one or more presence sensors within the enclosed space. The presence sensors are configured to detect a presence of an individual within the enclosed space.

The UV light assembly may be linearly moved between the deployed position and the stowed position. Optionally, the UV light assembly may be rotatably or pivotally moved between the deployed position and the stowed position. In this regard, it will be understood that the UV light assembly may be moved between the deployed position and the stowed position by a mechanism having one or more axes or degrees of freedom.

In at least one embodiment, the UV light assembly is rotatably moved about a longitudinal axis in the deployed position during a sanitizing cycle. Optionally, the UV light assembly may be pivotally moved about an end in the deployed position during a sanitizing cycle.

Certain embodiments of the present disclosure provide a UV light sanitizing method that is configured to sanitize at least one surface within an enclosed space. The UV light sanitizing method includes selectively moving a UV light assembly between a stowed position and a deployed position. The selectively moving includes stowing the UV light assembly within a stowage chamber connected to the enclosed space in the stowed position, and deploying the UV light assembly out of the stowage chamber and into the enclosed space in the deployed position.

Certain embodiments of the present disclosure provide an aircraft that includes an internal cabin, and a lavatory within the internal cabin. The lavatory includes a floor that supports a toilet and a sink. At least one ultraviolet (UV) light sanitizing system is configured to sanitize at least one surface of the floor, the toilet, or the sink.

DETAILED DESCRIPTION OF THE DISCLOSURE

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Certain embodiments of the present disclosure provide a system and method for deploying a UV light assembly during a sanitizing cycle. In at least one embodiment, the system includes an articulating, shielded, UV lamp that is configured to emit far UV light onto a component, such as a toilet or sink within an aircraft lavatory. The UV lamp is secured in a stowed position when not in use, such as when an individual is within a lavatory.

When a sanitizing cycle is initiated, the UV light assembly is deployed through an aperture formed through a wall within a lavatory. The UV light assembly is actuated into a deployed position, at which UV light is emitted onto a component (such as a toilet). In at least one embodiment, the UV light assembly includes a shield, such as a Faraday cage or screen positioned over and/or around at least a portion of a UV light emitter. The shield is configured to reduce electromagnetic interference (EMI) that may otherwise be generated by the UV light emitter. In the deployed position, the UV light assembly is in close proximity to the component being sanitized, such as a distance between 1-5 inches, although the distance may be lesser or greater. In the deployed position, the UV light assembly is closer to a component that is to be sterilized as compared to the stowed position. By positioning the UV light assembly in close proximity to the component to be sterilized, an overall time of a sanitizing cycle is reduced.

Certain embodiments of the present disclosure provide a sanitizing system that includes a UV light assembly that is stowable in a chamber within or connected to a monument. The sanitizing system may include an actuator operatively coupled to the UV light assembly through an articulator, such as an arm, bracket, beam, or other such link. Optionally, the actuator may be directly coupled to the UV light assembly without the use of a separate articulator. As a sanitizing cycle is initiated, the actuator deploys the UV light assembly into a deployed position, at which the UV light assembly is in close proximity to a surface to be sanitized. The surface may be a portion of a component, such as a floor, toilet, sink, or the like within a lavatory of an aircraft. In at least one embodiment, the UV light assembly is deactivated and in a stowed position when the monument (such as a lavatory) is occupied by an individual.

Certain embodiments of the present disclosure provide a method of sanitizing a surface within a lavatory that includes closing a lavatory door, determining that the interior of the lavatory is unoccupied, deploying a UV light assembly from a stowage chamber, positioning the UV light assembly in close proximity to the surface, and emitting UV light from the UV light assembly onto the surface for a predetermined sanitizing period. Upon completion of the sanitizing period, the method may also include stowing the UV light assembly into the stowage chamber.

Figure 1:
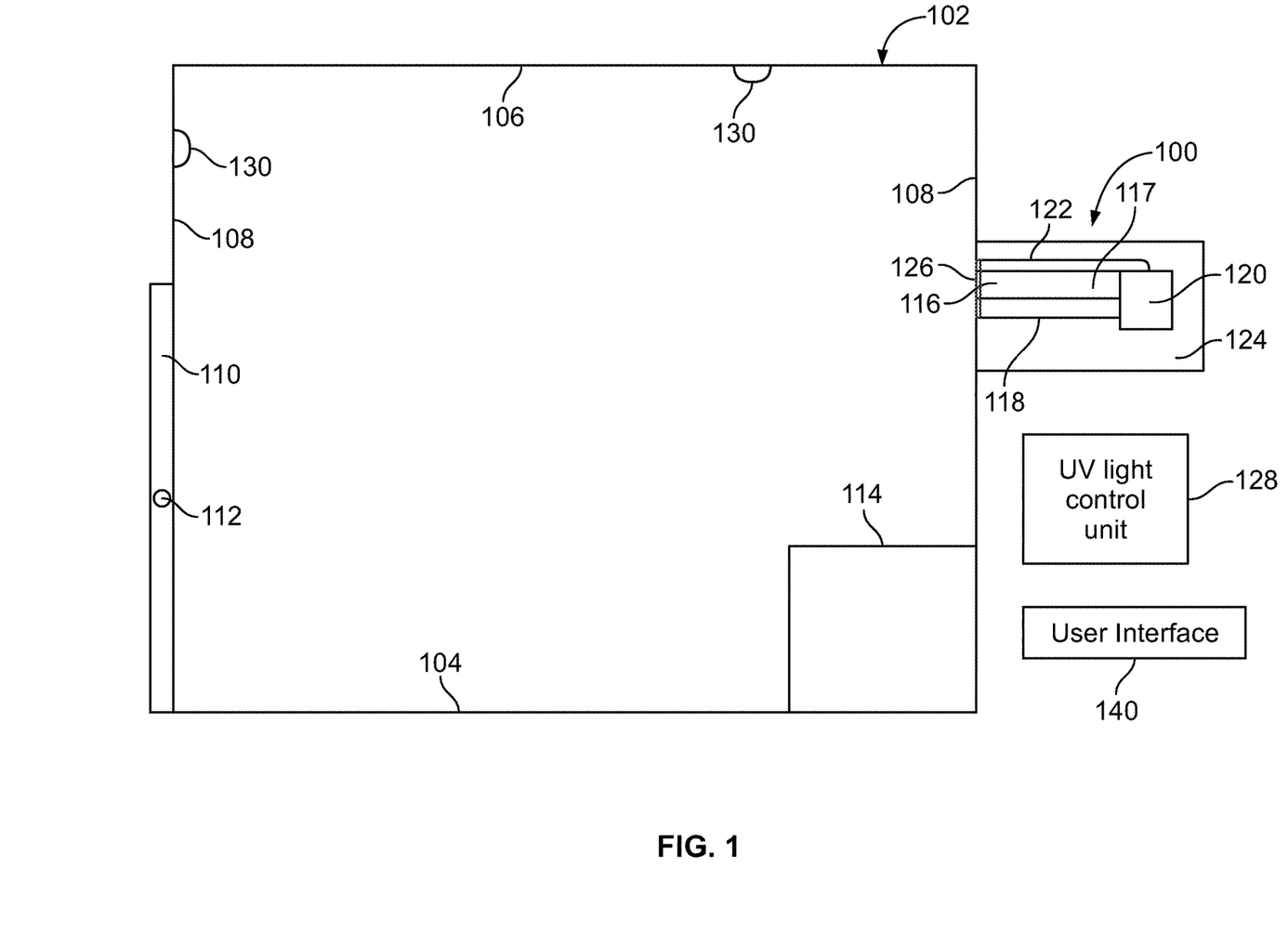
FIG. 1 illustrates a schematic diagram of an ultraviolet light sanitizing system for an enclosed space, according to an embodiment of the present disclosure.

FIG. 1 illustrates a schematic diagram of a UV light sanitizing system 100 for an enclosed space 102, according to an embodiment of the present disclosure. The enclosed space 102 may be defined by a floor 104, a ceiling 106, and walls 108 extending between the floor 104 and the ceiling 106. A door 110 may be moveably secured to one of the walls 108. The door 110 includes a lock 112 that is configured to securely lock the door 110 in a closed position. When the lock 112 is in a locked position, the door 110 is unable to be opened. When the lock 112 is in an unlocked position, the door 110 may be opened. The enclosed space 102 may be a confined space onboard a commercial aircraft. For example, the enclosed space 102 may be a lavatory onboard an aircraft. As another example, the enclosed space 102 may be a galley onboard an aircraft. As yet another example, the enclosed space 102 may be a passenger cabin onboard an aircraft. The enclosed space 102 may or may not include the door 110. The enclosed space 102 may be within various other vehicles, structures, and/or the like. For example, the enclosed space 102 may be a room within a commercial, municipal, or residential building, or a room onboard a train, bus, ship, or the like.

The enclosed space 102 includes at least one structure 114 to be sanitized (for example, disinfected, sterilized, or otherwise cleaned) after use. For example, the structure 114 may be a toilet, sink, floor, cabinet, and/or the like within a lavatory of an aircraft.

The UV light sanitizing system 100 includes a UV light assembly 116 that includes a housing 117 and a UV light emitter 118. The UV light emitter 118 may include one or more UV light elements, such as an arc lamp(s), laser(s), light emitting diode(s) (LEDs), microfilament(s), fiber optic element(s), bulb(s), and/or the like. In at least one embodiment, the sanitizing UV light is far UV light. Alternatively, the sanitizing UV light may be UVA light, UVB light, UVC light, vacuum UV light, or the like. In at least one embodiment, the UV light assembly 116 may include UV light elements that are configured to emit UV light with different UV bands (for example, at different wavelengths and different frequencies). For example, one UV light element may be configured to emit far UV light, while another UV light element may be configured to emit UVC light.

An actuator 120 may be operatively coupled to the UV light assembly 116 through an articulator 122. The actuator 120 may be an electric motor, a pneumatic motor, a hydraulic motor, one or more solenoids, one or more pistons, and/or the like that is configured to selectively move the UV light assembly 116 between a stowed position (as shown in FIG. 1) and a deployed position, in which the UV light emitter 118 is in close proximity (for example, between 1-5 inches) to a surface of the component 114 that is to be sanitized.

The articulator 122 may be an arm, bracket, beam, and/or the like that operatively couples the actuator 120 to the UV light assembly 116. For example, the articulator 122 may be a robotic arm having an end effector that securely couples to the UV light assembly 116. Optionally, the actuator 120 may be directly coupled to the UV light assembly 116 without a separate and distinct articulator.

In the stowed position, the UV light assembly 116 is positioned within a stowage chamber 124 connected to a wall 108 of the enclosed space 102. An aperture 126 (such as a hole, channel, or other such opening) is formed through the wall 108 and connects to the stowage chamber 124. Optionally, the stowage chamber 124 may be formed in other walls 108 than shown, the ceiling 106, or the floor 104.

A UV light control unit 128 is coupled to and in communication with the actuator 120 and the UV light assembly 116, such as through one or more wired or wireless connections. The UV light control unit 128 may be positioned within or connected to the enclosed space 102, or may be remotely located therefrom. In at least one embodiment, the UV light control unit 128 is housed within the UV light assembly 116. The UV light control unit 128 is configured to control operation of the actuator 120 and the UV light assembly 116 to selectively deploy and stow the UV light assembly 116 into deployed and stowed positions.

One or more presence sensors 130 may be secured within the enclosed space 102. The presence sensors 130 may be ultrasound sensors, infrared sensors, thermal sensors, and/or the like that are configured to detect the presence of an individual within the enclosed space. In at least one embodiment, at least one presence sensor 130 may be a digital scale that detects the presence of an individual through a discernable detection of mass or weight within the enclosed space 102. The presence sensors 130 are in communication with the UV light control unit 128 through one or more wired or wireless connections. Based on presence signals received from the presence sensors 130, the UV light control unit 128 determines whether or not an individual is within the enclosed space 102. When the UV light control unit 128 determines that an individual is within the enclosed space, the UV light control unit 128 refrains from deploying the UV light assembly 126 and activating a sanitizing cycle.

Optionally, the enclosed space 102 may not include the presence sensors 130. Instead, the UV light control unit 128 may be configured to determine that the enclosed space is unoccupied, such as by being in communication with the lock 112 and/or the component 114. For example, the UV light control unit 128 may determine that the enclosed space 102 is unoccupied when the door 110 is locked. The UV light control unit 128 may initiate a sanitizing cycle based on a sequence of events, which may be triggered by the component 114 being used, the door being unlocked, and the door being subsequently closed. During the sanitizing cycle, when the UV light assembly 116 is moved into the deployed position and emitting UV light onto a surface within the enclosed space 102, the UV light control unit 128 may ensure that the door 110 is locked, so that individuals may not enter the enclosed space 102. As the sanitizing cycle complete, the UV light control unit 128 deactivates the UV light emitter 118, operates the actuator 120 to move the UV light assembly 116 back into the stowage chamber 124, and then unlocks the door 110. In at least one embodiment, if the door 110 is opened, and/or the presence sensors 130 detect the presence of an individual within the enclosed space 102 during a sanitizing cycle, the UV light control unit 130 may immediately cease operation of the UV light assembly 116, and return the UV light assembly 116 to the stowed position.

As noted, in operation, the UV light control unit 128 operates the actuator 120 to deploy the UV light assembly into a deployed position and activates the UV light emitter 118 during a sanitizing cycle when the enclosed space is unoccupied. Data regarding the sanitizing cycle is stored within a memory, such as within the UV light control unit 128 or coupled thereto. After the sanitizing cycle is completed, the UV light control unit 128 deactivates the UV light emitter 118 and operates the actuator 120 to retract the UV light assembly 116 back into the stowage chamber 124.

The UV light control unit 128 may initiate the sanitizing cycle after each use of the enclosed space (such as after each time the door 110 is locked and unlocked, and/or after each time the presence sensors 130 detect that an individual has left the enclosed space 102). Optionally, the sanitizing cycle may be initiated after a predetermined number of uses of the enclosed space 102, such as after each second, third, fourth, fifth, or nth use.

The UV light control unit 128 may also be in communication with a user interface 140, such as a computing device (for example, a computer, handheld smart device, dedicated control panel, or the like) that allows an individual (such as a flight attendant onboard an aircraft) to initiate the sanitizing cycle. Optionally, the UV light sanitizing system 100 may not include the user interface 140.

While the UV light sanitizing system 100 is shown with a single UV light assembly 116, additional UV light assemblies operatively coupled to actuators and selectively moveable between stowed and deployed positions may be used. For example, the UV light sanitizing system 100 may include two, three, four, or more deployable UV light assemblies and respective actuators that are in communication with the UV light control unit 128. Each UV light assembly may be configured to sanitize a different (or the same) surface within the enclosed space 102. For example, one UV light assembly may be configured to sanitize a surface of a toilet, another UV light assembly may be configured to sanitize a sink, while another UV light assembly may be configured to sanitize at least a portion of the floor 104.

As described, the UV light assembly 116 is selectively moveable between the stowed position and the deployed position. The UV light assembly 116 is stowed within the stowage chamber 124, which is connected to the enclosed space 102, when in the stowed position. The UV light assembly 116 deploys out of the stowage chamber 124 and into the enclosed space 102 in the deployed position.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the UV light control unit 128 may be or include one or more processors that are configured to control operation of the UV light assembly 116 and the actuator 120, as described above.

The UV light control unit 128 is configured to execute a set of instructions that are stored in one or more data storage units or elements (such as one or more memories), in order to process data. For example, the UV light control unit 128 may include or be coupled to one or more memories. The data storage units may also store data or other information as desired or needed. The data storage units may be in the form of an information source or a physical memory element within a processing machine.

The set of instructions may include various commands that instruct the UV light control unit 128 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the UV light control unit 128. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the UV light control unit 128 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
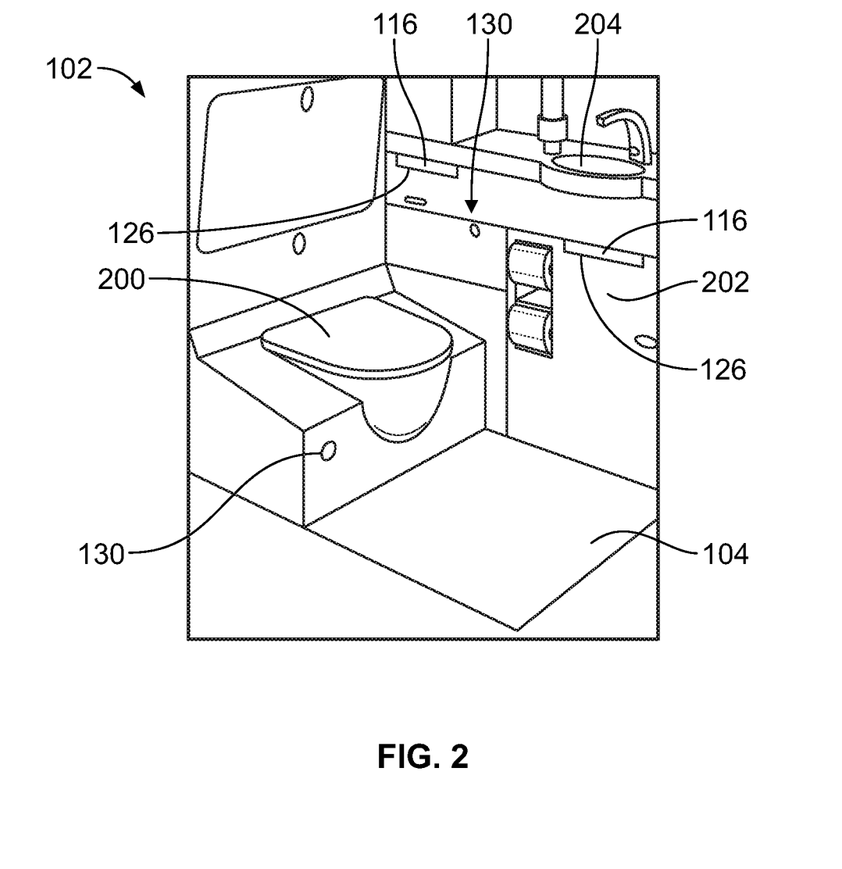
FIG. 2 illustrates a perspective internal view of a lavatory, according to an embodiment of the present disclosure.

FIG. 2 illustrates a perspective internal view of a lavatory 102, according to an embodiment of the present disclosure. The lavatory 102 is an example of the enclosed space 102 shown and described with respect to FIG. 1. The lavatory 102 may be onboard an aircraft, as described above. Optionally, the lavatory 102 may be onboard various other vehicles. In other embodiments, the lavatory 102 may be within a fixed structure, such as a commercial or residential building.

The lavatory 102 includes the floor 104 that supports a toilet 200, cabinets 202, and a sink 204. UV light assemblies 116 are secured within the lavatory 102 and are configured to be activated during a sanitizing cycle to sanitize (for example, disinfect, sterilize, or otherwise clean) various structures within the lavatory 102, such as the toilet 200, the floor 104, the cabinets 202, and/or the sink 204. The presence sensors 130 may be secured to portions of the lavatory 102.

As shown in FIG. 2, the UV light assemblies 116 are shown in stowed positions, such that each is recessed within a respective stowage chamber (hidden from view) connected to apertures 126. Outer wall portions of the UV light assemblies 116 may fit within the apertures 126 to provide an unobtrusive, flush, and smooth interface with portions of the lavatory 102 that define the apertures 126. In at least one other embodiment, a separate and distinct covering member (such as a spring-biased flap, wall portion, panel, or the like) may cover an aperture 126 when the UV light assemblies 116 are in the stowed positions.

Figure 3:
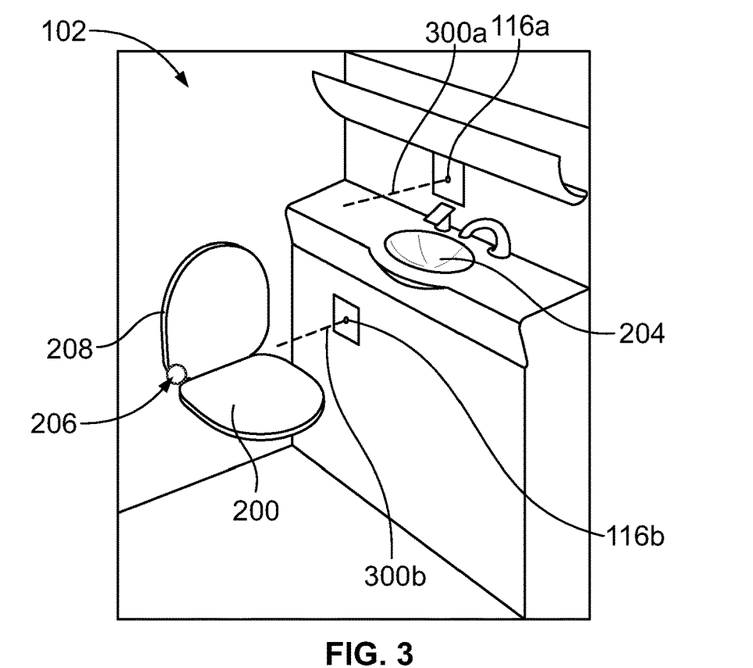
FIG. 3 illustrates a perspective internal view of a lavatory with UV light assemblies in stowed positions, according to an embodiment of the present disclosure.

FIG. 3 illustrates a perspective internal view of the lavatory 102 with UV light assemblies 116a and 116b in stowed positions, according to an embodiment of the present disclosure. The UV light assembly 116a is configured to sanitize the sink 204, while the UV light assembly is configured to sanitize the toilet 200.

Referring to FIGS. 1 and 3, in at least one embodiment, the UV light control unit 128 is in communication with an actuator 206 that is operatively coupled to a covering seat 208 of the toilet 200. As the sanitizing cycle is initiated, the UV light control unit 128 operates the actuator 206 to automatically open the covering seat 208. Optionally, the UV light control unit 128 does not open the covering seat 208 as the sanitizing cycle is initiated.

Figure 4:
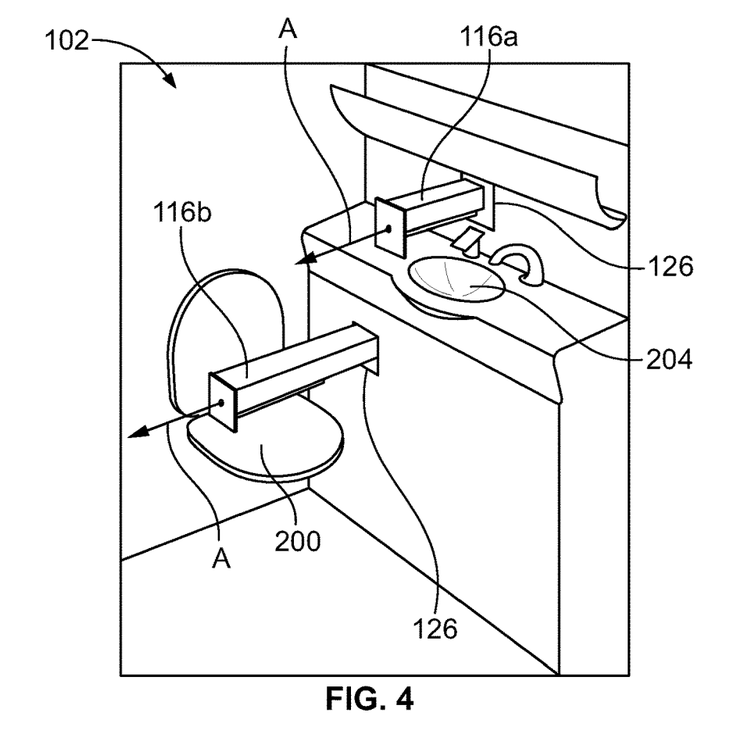
FIG. 4 illustrates a perspective internal view of a lavatory with UV light assemblies in deployed positions, according to an embodiment of the present disclosure.

FIG. 4 illustrates a perspective internal view of the lavatory with the UV light assemblies 116a and 116b in deployed positions, according to an embodiment of the present disclosure. Referring to FIGS. 1, 3, and 4, during the sanitizing cycle, the UV light control unit 128 operates the actuators 120 coupled to the UV light assemblies 116a and 116a to deploy out of their respective stowage chambers 124 and into close proximity with the sink 204 and the toilet 200, respectively. As shown, the UV light assemblies 116a and 116b are actuated into deployed positions in linear directions A that are parallel to longitudinal axes of the UV light assemblies 116a and 116b. The UV light assemblies 116a and 116b linearly deploy out of the stowage chambers 124 into the deployed positions. After the sanitizing cycle is complete, the UV light control unit 128 controls the actuators 120 to linearly retract the UV light assemblies back into their respective stowage chambers 124.

Figure 5:
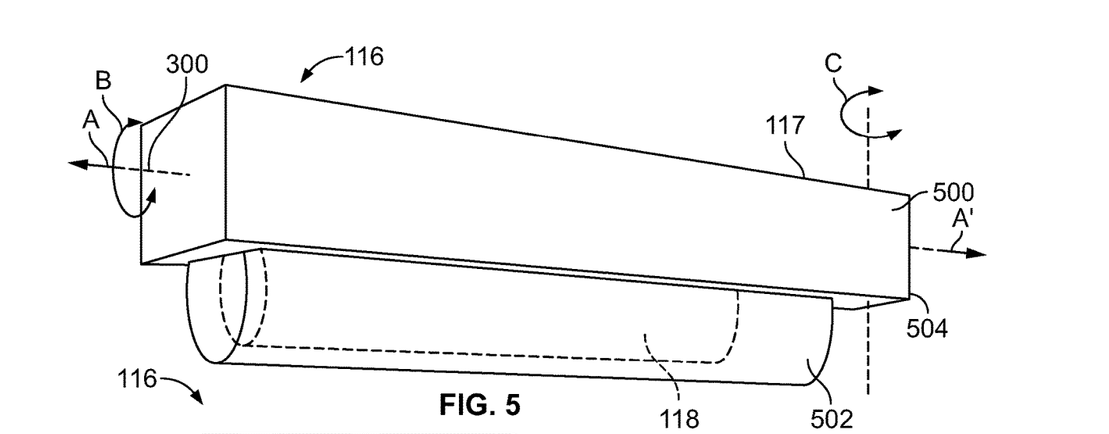
FIG. 5 illustrates a perspective lateral view of a UV light assembly, according to an embodiment of the present disclosure.
Figure 6:
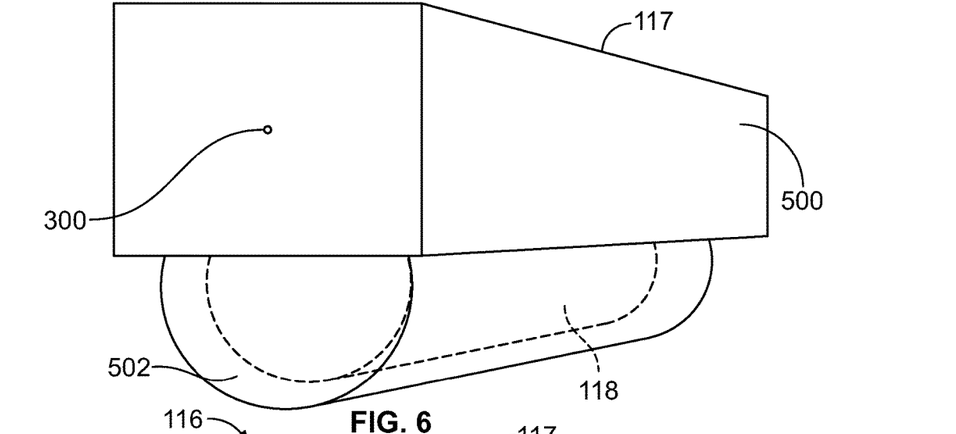
FIG. 6 illustrates a perspective end view of a UV light assembly, according to an embodiment of the present disclosure.
Figure 7:
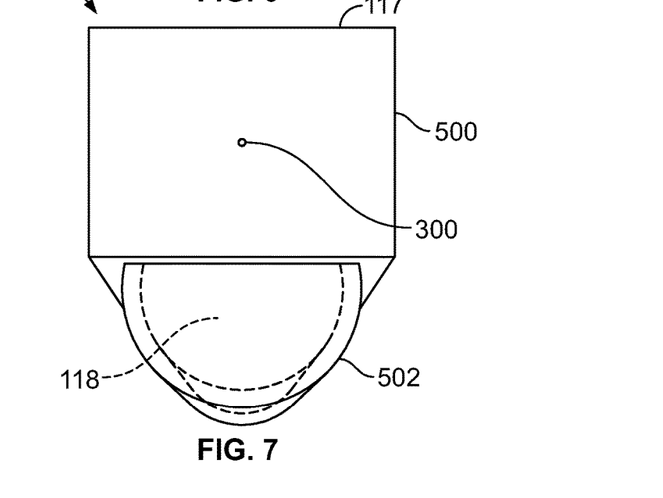
FIG. 7 illustrates an end view of a UV light assembly, according to an embodiment of the present disclosure.

FIG. 5 illustrates a perspective lateral view of a UV light assembly 116, according to an embodiment of the present disclosure. FIG. 6 illustrates a perspective end view of the UV light assembly 116. FIG. 7 illustrates an end view of the UV light assembly 116. Referring to FIGS. 5-7, the light emitter 118 may be an arc lamp that is configured to emit far UV light. An arc lamp may generate EMI, which may interfere with various electronic and electrical systems, such as onboard an aircraft. Accordingly, the housing 117 may include an EMI shield 500 (such as a metal housing or cover), while a Faraday cage 502 may be secured around the light emitter 118. The Faraday cage 502 includes a wire screen having openings that allow emitted UV light to pass therethrough. Alternatively, the UV light assembly 116 may not include the EMI shield and/or the Faraday cage 502, such as if the UV light assembly 116 is used within an enclosed space in which there are few, if any, electronic or electrical components in close proximity thereto.

Referring to FIGS. 3-5, the UV light assembly 116 is moved into the deployed state in a linear direction A that is parallel to the longitudinal axis 300 of the UV light assembly 116. The UV light assembly 116 is moved back into the stowed state in an opposite linear direction A' that is parallel to the longitudinal axis 300.

Figure 8:
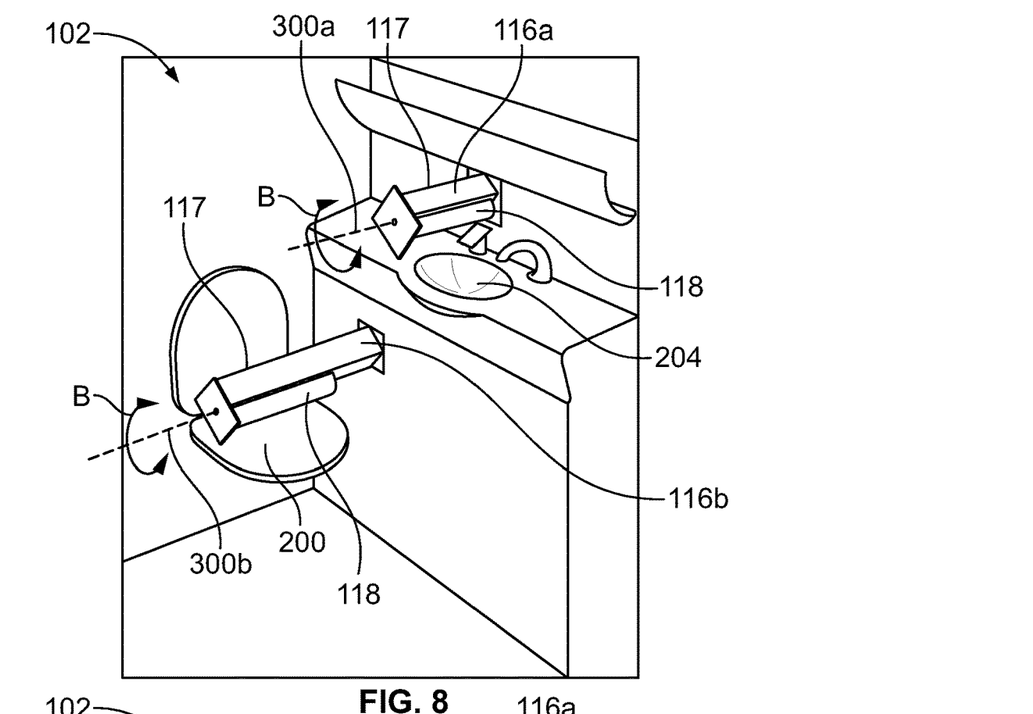
FIG. 8 illustrates a perspective internal view of a lavatory with UV light assemblies in deployed positions, according to an embodiment of the present disclosure.

FIG. 8 illustrates a perspective internal view of the lavatory with the UV light assemblies 116a and 116b in deployed positions, according to an embodiment of the present disclosure. Referring to FIGS. 1, 4, 5, and 8, in the deployed state and during the sanitizing cycle, the UV light control unit 128 may operate the actuators 120 to rotate (such as a rotation through a 90 degree radial arc) the UV light assemblies 116a and 116b about their respective longitudinal axes in the directions of arc B, in order to sweep emitted UV light over the sink 204 and the toilet 200.

Figure 9:
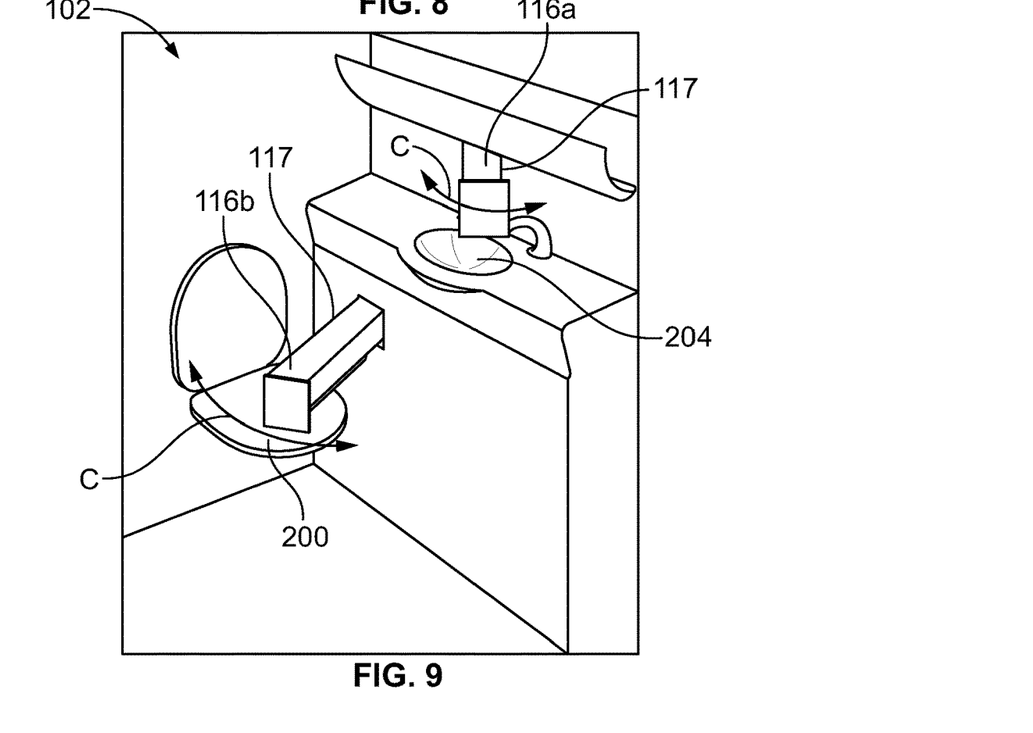
FIG. 9 illustrates a perspective internal view of a lavatory with UV light assemblies in deployed positions, according to an embodiment of the present disclosure.

FIG. 9 illustrates a perspective internal view of the lavatory 102 with the UV light assemblies 116a and 116b in deployed positions, according to an embodiment of the present disclosure. Referring to FIGS. 1, 4, 5, and 9, in the deployed state and during the sanitizing cycle, the UV light control unit 128 may operate the actuators 120 to pivot the UV light assemblies 116a and 116b about respective ends 504 in the directions of arc C, in order to pivot emitted UV light over the sink 204 and the toilet 200. In at least one embodiment, the UV light assemblies 116a and 116b may be rotated as shown in FIG. 8, as well as pivoted as shown in FIG. 9.

Figure 10:
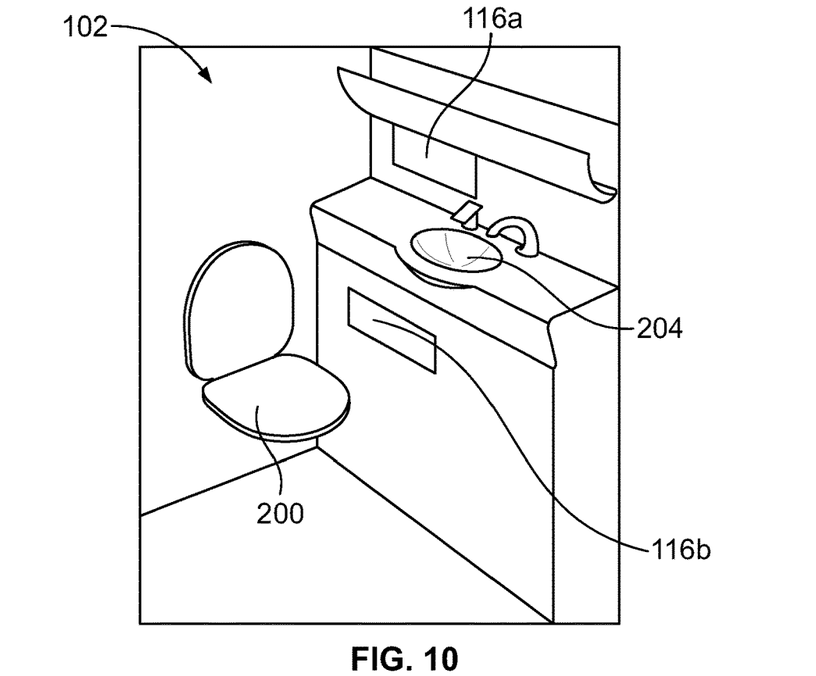
FIG. 10 illustrates a perspective internal view of a lavatory with UV light assemblies in stowed positions, according to an embodiment of the present disclosure.
Figure 11:
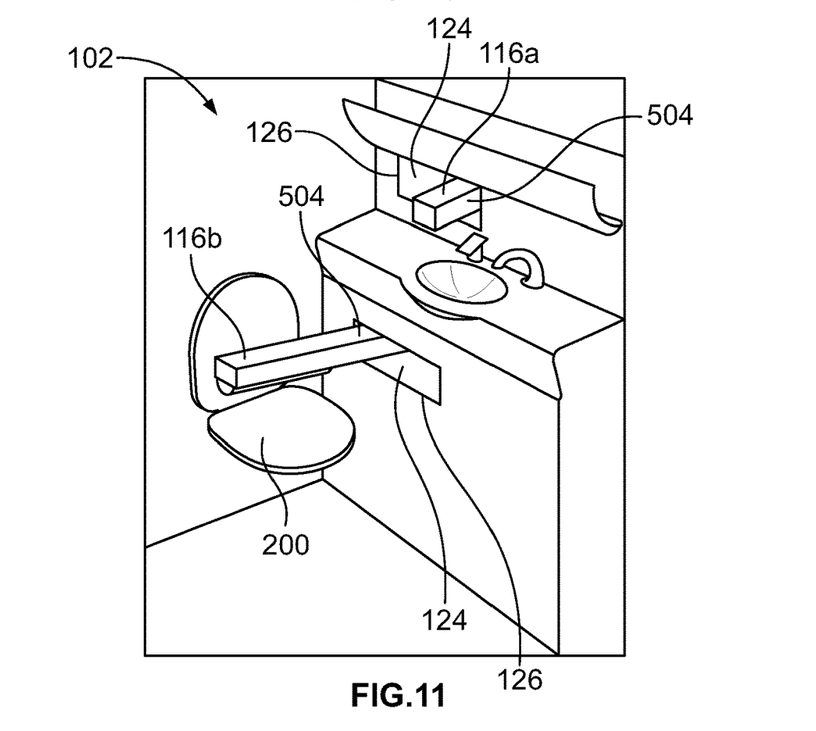
FIG. 11 illustrates a perspective internal view of a lavatory with UV light assemblies in deployed positions, according to an embodiment of the present disclosure.

FIG. 10 illustrates a perspective internal view of the lavatory 102 with UV light assemblies 116a and 116b in stowed positions, according to an embodiment of the present disclosure. FIG. 11 illustrates a perspective internal view of the lavatory with the UV light assemblies 116a and 116b in deployed positions. Referring to FIGS. 1, 10, and 11, respective ends 504 of the UV light assemblies 116a and 116 are pivotally secured within the stowage chambers 124. During deployment, the UV light control unit 128 operates the actuators 120 to pivot the UV light assemblies 116a and 116b out of the stowage chambers about vertical pivot axes of the ends 504, which are operatively coupled to the actuators 120.

Figure 12:
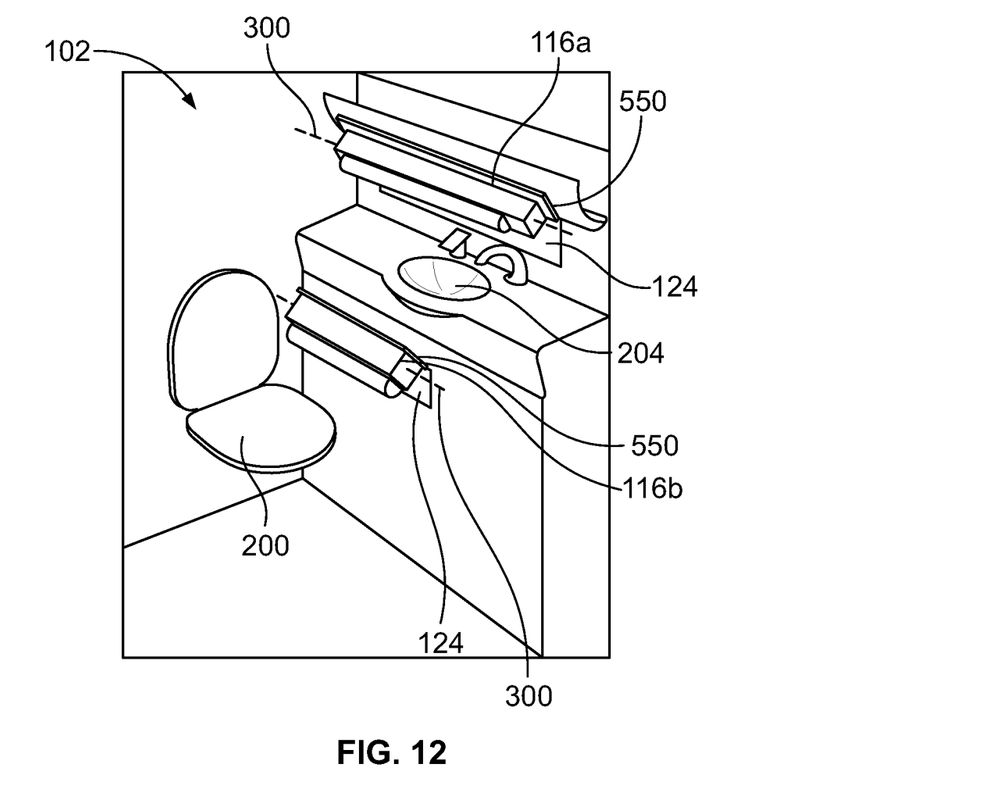
FIG. 12 illustrates a perspective internal view of a lavatory with UV light assemblies in deployed positions, according to an embodiment of the present disclosure.

FIG. 12 illustrates a perspective internal view of the lavatory 102 with UV light assemblies 116a and 116b in deployed positions, according to an embodiment of the present disclosure. As shown, the UV light assemblies 116a and 116b may be pivotally coupled to the lavatory 102 through pivot axles 550, which may be or include hinges or the like. The pivot axles 550 are parallel with the longitudinal axes 300 of the UV light assemblies 116a and 116b. The actuators 120 are operated to pivot the UV light assemblies 116a and 116b into the deployed positions by pivoting the UV light assemblies 116a and 116b about their respective pivot axles 550.

Figure 13:
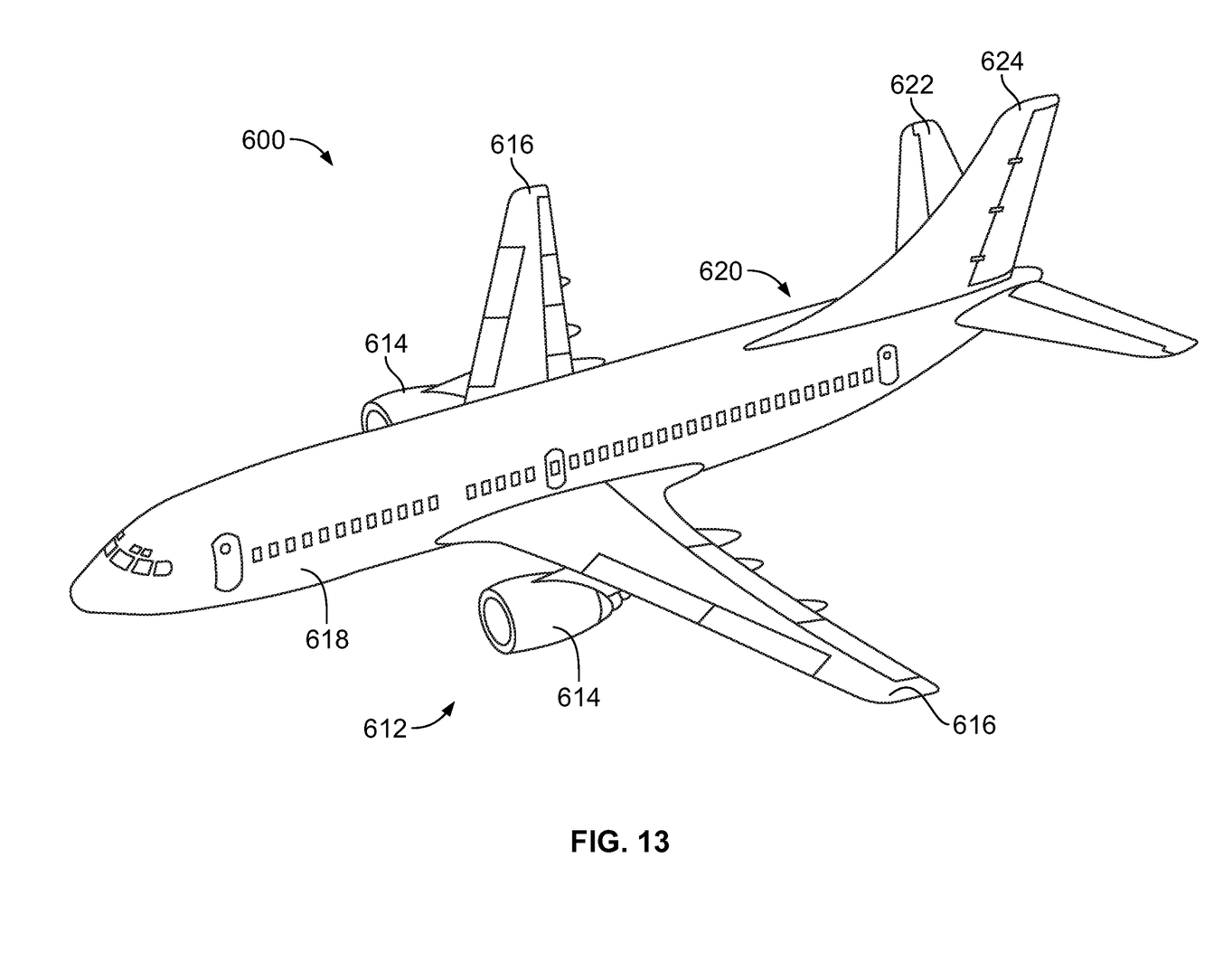
FIG. 13 illustrates a perspective top view of an aircraft, according to an embodiment of the present disclosure.

FIG. 13 illustrates a perspective top view of an aircraft 600, according to an embodiment of the present disclosure. The aircraft 600 includes a propulsion system 612 that may include two turbofan engines 614, for example. Optionally, the propulsion system 612 may include more engines 614 than shown. The engines 614 are carried by wings 616 of the aircraft 600. In other embodiments, the engines 614 may be carried by a fuselage 618 and/or an empennage 620. The empennage 620 may also support horizontal stabilizers 622 and a vertical stabilizer 624.

The fuselage 618 of the aircraft 600 defines an internal cabin, which may include a cockpit, one or more work sections (for example, galleys, personnel carry-on baggage areas, and the like), one or more passenger sections (for example, first class, business class, and coach sections), and an aft section in which an aft rest area assembly may be positioned. Each of the sections may be separated by a cabin transition area, which may include one or more class divider assemblies. Overhead stowage bin assemblies may be positioned throughout the internal cabin. The internal cabin includes one or more chambers, such as lavatories, for example. One or more UV light sanitizing systems 100 (shown and described with respect to FIG. 1) may be located within the internal cabin.

Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 14:
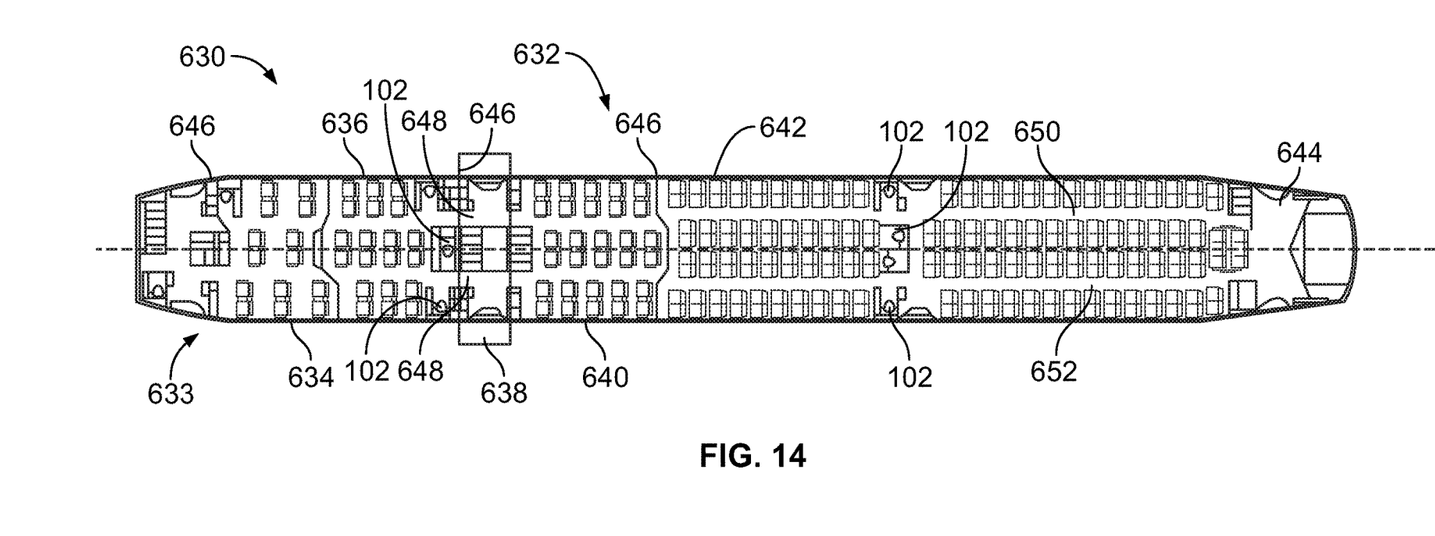
FIG. 14 illustrates a top plan view of an internal cabin of an aircraft, according to an embodiment of the present disclosure.

FIG. 14 illustrates a top plan view of an internal cabin 630 of an aircraft, according to an embodiment of the present disclosure. The internal cabin 630 may be within a fuselage 632 of the aircraft. For example, one or more fuselage walls may define the internal cabin 630. The internal cabin 630 includes multiple sections, including a front section 633, a first class section 634 (or first class suites, cabins, for example), a business class section 636, a front galley station 638, an expanded economy or coach section 640, a standard economy or coach section 642, and an aft section 644, which may include multiple enclosed spaces or chambers 102, such as lavatories and galley stations. It is to be understood that the internal cabin 630 may include more or less sections than shown. For example, the internal cabin 630 may not include a first class section, and may include more or less galley stations than shown. Each of the sections may be separated by a cabin transition area 646, which may include class divider assemblies between aisles 648.

As shown in FIG. 14, the internal cabin 630 includes two aisles 650 and 652 that lead to the aft section 644. Optionally, the internal cabin 630 may have less or more aisles than shown. For example, the internal cabin 630 may include a single aisle that extends through the center of the internal cabin 630 that leads to the aft section 644.

One or more enclosed spaces 102, such as lavatories, may be located within the internal cabin 630. UV light sanitizing systems 100 may be used to sanitize structures within the lavatories 102, such as described above.

Figure 15:
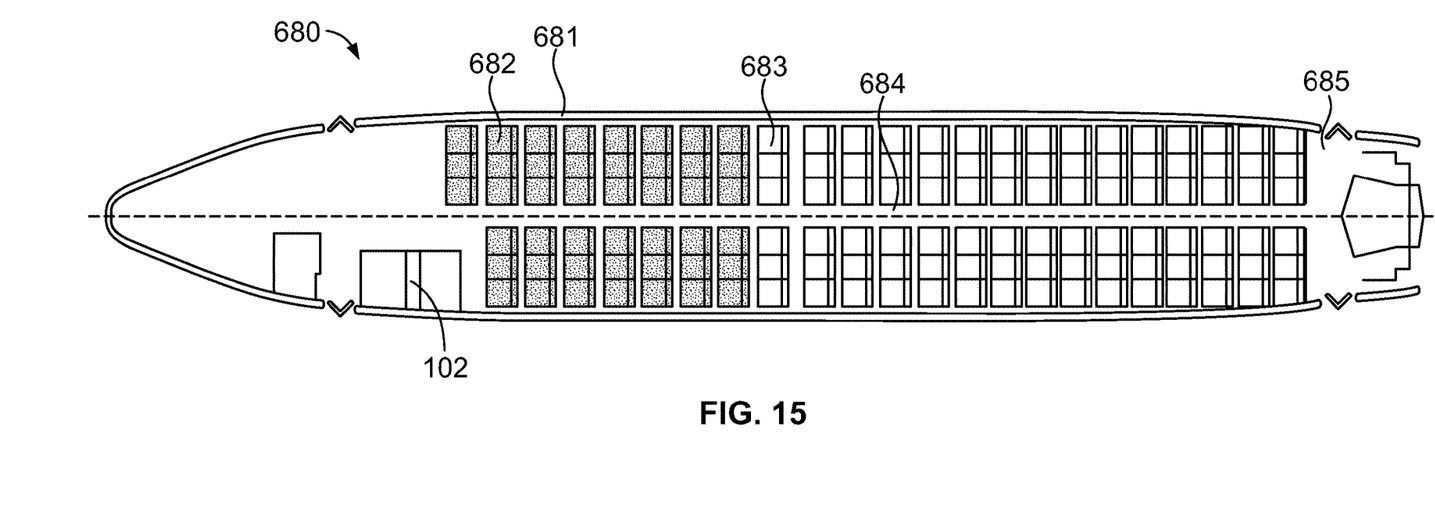
FIG. 15 illustrates a top plan view of an internal cabin of an aircraft, according to an embodiment of the present disclosure.

FIG. 15 illustrates a top plan view of an internal cabin 680 of an aircraft, according to an embodiment of the present disclosure. The internal cabin 680 may be within a fuselage 681 of the aircraft. For example, one or more fuselage walls may define the internal cabin 680. The internal cabin 680 includes multiple sections, including a main cabin 682 having passenger seats 683, and an aft section 685 behind the main cabin 682. It is to be understood that the internal cabin 680 may include more or less sections than shown.

The internal cabin 680 may include a single aisle 684 that leads to the aft section 685. The single aisle 684 may extend through the center of the internal cabin 680 that leads to the aft section 685. For example, the single aisle 684 may be coaxially aligned with a central longitudinal plane of the internal cabin 680.

One or more enclosed spaces 102, such as lavatories, may be located within the internal cabin 680. UV light sanitizing systems 100 may be used to sanitize structures within the lavatories 102, such as described above.

Figure 16:
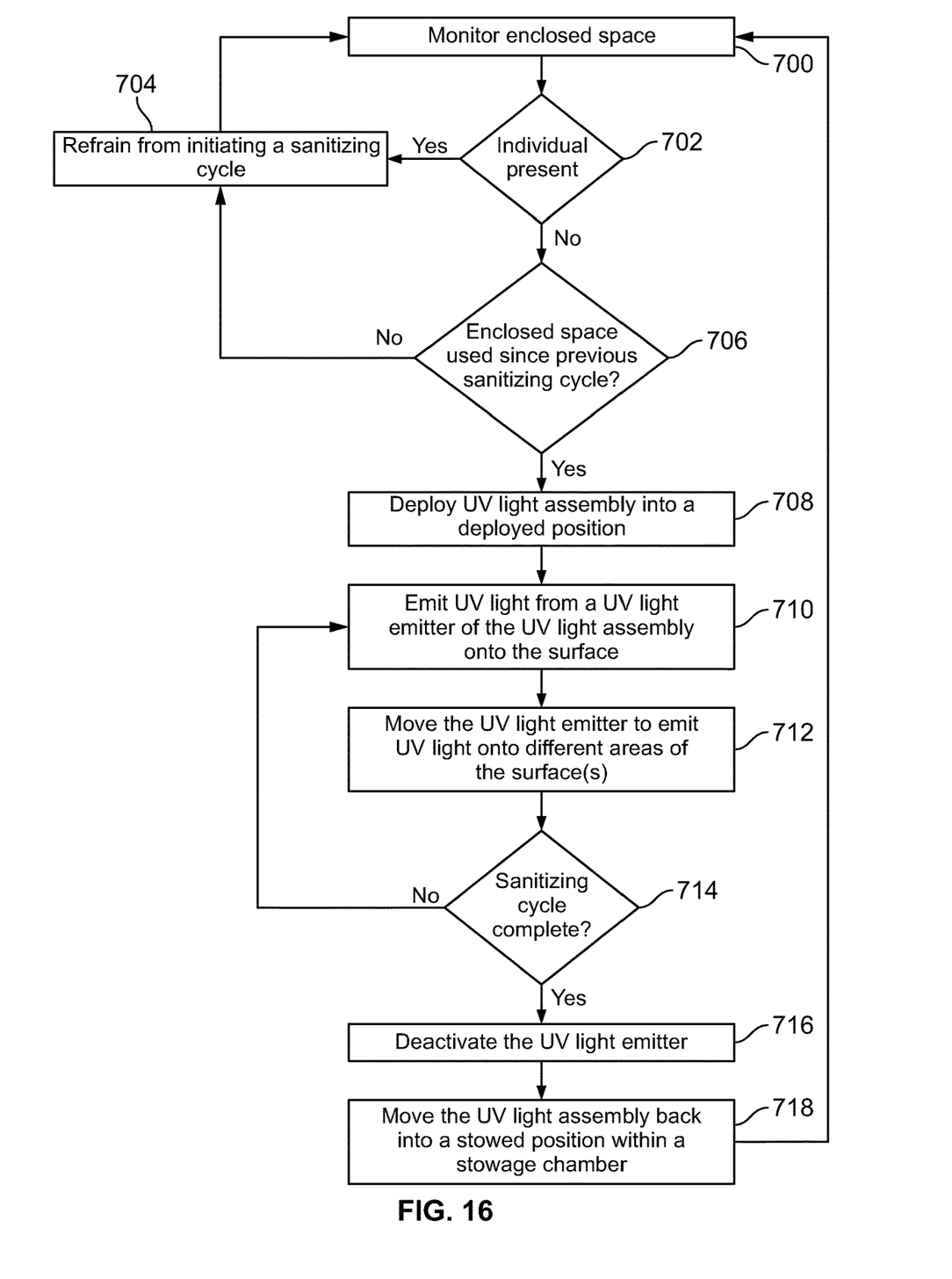
FIG. 16 illustrates a flow chart of a method of sanitizing one or more surfaces within an enclosed space, according to an embodiment of the present disclosure.

FIG. 16 illustrates a flow chart of a method of sanitizing one or more surfaces within an enclosed space, according to an embodiment of the present disclosure. Referring to FIGS. 1 and 16, the method begins at 700, at which the enclosed space 102 is monitored, such as by the UV light control unit 128 receiving presence signals from the presence sensors 130, and/or lock signals received from the door 110 and/or the lock 112.

At 702, the UV light control unit 128 determines if an individual is present within the enclosed space 102. If an individual is present, the method proceeds to 704, in which the UV light control unit 128 refrains from initiating a sanitizing cycle 704. The method then returns to 700.

If, however, the UV light control unit 128 determines that an individual is not present within the enclosed space 102, the method proceeds to 706, at which the UV light control unit 128 determines whether the enclosed space has been used since a previous sanitizing cycle 706. For example, the UV light control unit 128 may determine that the enclosed space 102 has not been used if signals received from the presence sensors 130, the door 110, and/or the lock 112 indicate that no one has entered the enclosed space 102 since a prior sanitizing cycle. If the UV light control unit 128 determines that the enclosed space has not been used since a previous sanitizing cycle, the method returns to 704.

If, however, the UV light control unit 128 determines that the enclosed space 102 has been used since a previous sanitizing cycle, the method proceeds from 706 to 708, at which the UV light control unit 128 operates the actuator 120 to deploy the UV light assembly 116 into a deployed position, thereby initiating a sanitizing cycle. Next, at 710, the UV light control unit 128 operates the UV light emitter 118 to emit UV light onto the surface(s) within the enclosed space 102. At 712, the UV light control unit 128 may operate the actuator 120 to move the UV light emitter so that the emitted UV light is moved onto different areas of the surface(s). Optionally, the method may not include 712. If at any time during the sanitizing cycle (from initial deployment through UV light emission), the UV light control unit 128 determines that an individual has entered the enclosed space 102, the UV light control unit 128 may control the UV light assembly 116 to immediately cease UV light emission, and operate the actuator 120 to return the UV light assembly 116 back into a stowed position.

At 714, the UV light control unit 128 determines whether the sanitizing cycle is complete. If the sanitizing cycle is not complete, the method returns to 710. If, however, the sanitizing cycle is complete, the method proceeds from 714 to 716, at which the UV light control unit 128 controls the UV light assembly 116 to deactivate the UV light emitter 118. Then, at 718, the UV light control unit 128 operates the actuator 120 to retract or otherwise move the UV light assembly 116 back into a stowed position within the stowage chamber 124. The method then returns to 700.

As described above, embodiments of the present disclosure provide systems and methods for efficiently and effectively sanitizing various surfaces within an enclosed space, such as a lavatory onboard a commercial aircraft. Embodiments of the present disclosure provide systems and methods for operating a UV light assembly to sanitize a component (such as toilet within a lavatory of an aircraft) without interfering with use of the component.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An ultraviolet (UV) light sanitizing system that is configured to sanitize at least one surface within an enclosed space, the UV light sanitizing system comprising:
 a UV light assembly that is selectively moveable between a stowed position and a deployed position, wherein the UV light assembly is stowed within a stowage chamber connected to the enclosed space in the stowed position, and wherein the UV light assembly deploys out of the stowage chamber and into the enclosed space in the deployed position, wherein the UV light assembly is linearly moved between the deployed position and the stowed position.

2. The UV light sanitizing system of claim 1, wherein the UV light assembly is closer to the at least one surface in the deployed position than the stowed position.

3. The UV light sanitizing system of claim 1, wherein the UV light assembly remains in the stowed position when the enclosed space is occupied by an individual.

4. The UV light sanitizing system of claim 1, wherein the UV light assembly comprises:
a housing;
a shield surrounding at least a portion of the housing, wherein the shield is configured to block electromagnetic interference;
a UV light emitter; and
a cage surrounding at least a portion of the UV light emitter.

5. The UV light sanitizing system of claim 1, further comprising an actuator operatively coupled to the UV light assembly, wherein the actuator is configured to move the UV light assembly between the stowed position and the deployed position.

6. The UV light sanitizing system of claim 1, further comprising a UV light control unit in communication with the UV light assembly, wherein the UV light control unit is configured control movement of the UV light assembly between the stowed position and the deployed position, and wherein the UV light control unit is configured to operate the UV light assembly during a sanitizing cycle in which the UV light assembly emits sanitizing UV light onto the at least one surface.

7. The UV light sanitizing system of claim 1, further comprising one or more presence sensors within the enclosed space, wherein the one or more presence sensors are configured to detect a presence of an individual within the enclosed space.

8. The UV light sanitizing system of claim 1, wherein the UV light assembly is rotatably moved about a longitudinal axis in the deployed position during a sanitizing cycle.

9. The UV light sanitizing system of claim 1, wherein the UV light assembly is pivotally moved about an end in the deployed position during a sanitizing cycle.

10. An aircraft comprising:
an internal cabin;
a lavatory within the internal cabin, wherein the lavatory comprises a floor that supports a toilet and a sink; and
at least on ultraviolet (UV) light sanitizing system that is configured to sanitize at least one surface of the floor, the toilet, or the sink, the at least one UV light sanitizing system comprising:
a UV light assembly that is selectively moveable between a stowed position and a deployed position, wherein the UV light assembly is stowed within a stowage chamber connected to the lavatory in the stowed position, wherein the UV light assembly deploys out of the stowage chamber and into the lavatory in the deployed position, wherein the UV light assembly is closer to the at least one surface in the deployed position than the stowed position, wherein the UV light assembly is linearly or rotatably moved between the deployed position and the stowed position, and wherein the UV light assembly comprises (a) a housing, (b) a shield surrounding at least a portion of the housing, wherein the shield is configured to block electromagnetic interference, (c) a UV light emitter, and (d) a cage surrounding at least a portion of the UV light emitter;
an actuator operatively coupled to the UV light assembly, wherein the actuator linearly moves the UV light assembly between the stowed position and the deployed position;
a UV light control unit in communication with the UV light assembly, wherein the UV light control unit is configured control movement of the UV light assembly between the stowed position and the deployed position, and wherein the UV light control unit is configured to operate the UV light assembly during a sanitizing cycle in which the UV light assembly emits sanitizing UV light onto the at least one surface, wherein the UV light assembly is rotatably moved about a longitudinal axis or pivotally moved about an end in the deployed position during the sanitizing cycle; and
one or more presence sensors within the lavatory and in communication with the UV light control unit, wherein the one or more presence sensors are configured to detect a presence of an individual within the lavatory, wherein the UV light control unit maintains the UV light assembly in the stowed position when the lavatory is occupied by an individual.

* * * * *